(12) United States Patent
Rouleau et al.

(10) Patent No.: US 8,292,927 B2
(45) Date of Patent: Oct. 23, 2012

(54) FLEXIBLE ARTICULATING SPINAL ROD

(75) Inventors: Jeffrey P Rouleau, Maple Grove, MN (US); Henry K Bonin, Jr., Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 262 days.

(21) Appl. No.: 12/429,368

(22) Filed: Apr. 24, 2009

(65) Prior Publication Data
US 2010/0274287 A1 Oct. 28, 2010

(51) Int. Cl.
*A61B 17/70* (2006.01)
(52) U.S. Cl. ........ 606/257; 606/254; 606/255; 606/258; 606/259
(58) Field of Classification Search ........... 606/246–279
See application file for complete search history.

(56) References Cited

U.S. PATENT DOCUMENTS

| | | | |
|---|---|---|---|
| 5,375,823 A | 12/1994 | Navas | |
| 5,480,401 A | 1/1996 | Navas | |
| 5,540,688 A | 7/1996 | Navas | |
| 5,562,737 A | 10/1996 | Graf | |
| 5,961,516 A | 10/1999 | Graf | |
| 7,029,475 B2 | 4/2006 | Panjabi | |
| 7,291,150 B2 | 11/2007 | Graf | |
| 7,326,210 B2 | 2/2008 | Jahng | |
| 7,476,238 B2 | 1/2009 | Panjabi | |
| 7,704,271 B2 | 4/2010 | Abdou | |
| 2003/0191470 A1 | 10/2003 | Ritland | |
| 2003/0220643 A1* | 11/2003 | Ferree | 606/61 |
| 2004/0049190 A1* | 3/2004 | Biedermann et al. | 606/61 |
| 2004/0236329 A1 | 11/2004 | Panjabi | |
| 2005/0049708 A1 | 3/2005 | Atkinson | |
| 2005/0131405 A1 | 6/2005 | Molz | |
| 2005/0131408 A1* | 6/2005 | Sicvol et al. | 606/61 |
| 2005/0165396 A1* | 7/2005 | Fortin et al. | 606/61 |
| 2005/0171540 A1 | 8/2005 | Lim | |
| 2005/0171543 A1 | 8/2005 | Timm | |
| 2005/0177156 A1 | 8/2005 | Timm | |
| 2005/0177157 A1 | 8/2005 | Jahng | |
| 2005/0177164 A1 | 8/2005 | Walters | |
| 2005/0177166 A1 | 8/2005 | Timm | |
| 2005/0182400 A1 | 8/2005 | White | |
| 2005/0182401 A1 | 8/2005 | Timm | |
| 2005/0182409 A1 | 8/2005 | Callahan | |
| 2005/0203517 A1 | 9/2005 | Jahng | |
| 2005/0203519 A1* | 9/2005 | Harms et al. | 606/61 |
| 2005/0222569 A1 | 10/2005 | Panjabi | |
| 2005/0245930 A1 | 11/2005 | Timm | |
| 2005/0277920 A1* | 12/2005 | Slivka et al. | 606/61 |
| 2005/0288670 A1 | 12/2005 | Panjabi | |
| 2006/0015100 A1 | 1/2006 | Panjabi | |
| 2006/0184171 A1* | 8/2006 | Biedermann et al. | 606/61 |
| 2006/0212033 A1* | 9/2006 | Rothman et al. | 606/61 |
| 2006/0247635 A1 | 11/2006 | Gordon | |
| 2006/0293657 A1 | 12/2006 | Hartmann | |
| 2007/0043356 A1 | 2/2007 | Timm | |
| 2007/0191841 A1 | 8/2007 | Justis | |
| 2007/0191845 A1 | 8/2007 | Justis | |
| 2007/0233073 A1 | 10/2007 | Wisnewski | |
| 2007/0270814 A1 | 11/2007 | Lim | |

(Continued)

*Primary Examiner* — Alvin Stewart
*Assistant Examiner* — Nicholas Plionis (57) ABSTRACT

Embodiments of the invention include a spinal construct for stabilizing a segment of a spinal column with a flexible spinal rod having one or more flexible components that articulate longitudinally and change curvature along at least a portion of their length in response to normal physiological loads.

20 Claims, 4 Drawing Sheets

U.S. PATENT DOCUMENTS

| | | |
|---|---|---|
| 2008/0183213 A1 | 7/2008 | Veldman |
| 2008/0228227 A1 | 9/2008 | Brown |
| 2008/0255616 A1 | 10/2008 | Atkinson |
| 2008/0312693 A1 | 12/2008 | Trautwein |
| 2009/0012562 A1* | 1/2009 | Hestad et al. ................. 606/246 |
| 2009/0082810 A1* | 3/2009 | Bhatnagar et al. ............ 606/250 |

* cited by examiner

FLEXIBLE ARTICULATING SPINAL ROD

FIELD OF THE INVENTION

The present invention relates generally to the field of medical implants, and more particularly relates to a flexible spinal rod that articulates to change length and changes curvature along at least a portion of its length in response to normal physiological loads.

BACKGROUND

Various pathologies of the human spine may be treated by stabilizing the joints of the spine. A traditional approach has been to rigidly fix joints of the spine through a number of surgical techniques and approaches. More recently, therapies have been developed to restore proper spacing of the spinal anatomy without more drastically affecting the natural motion of the spine by rigidly fixing or fusing one or more spinal joints. These therapies are sometimes referred to as motion preserving or dynamic, or as joint replacements, when specific joints such as joints between vertebral bodies or facet joints are replaced or treated. However, there remains a significant need to effectively mimic the natural load bearing and dynamic characteristics of the complex structure of the human spine.

A significant challenge associated with implementing systems with flexible and/or articulating components is providing adequate fixation to the anatomy while simultaneously mimicking characteristics of the spine under various loading and motion conditions such as flexion, extension, and lateral bending. It may be particularly challenging to design a system that can support all loads developed over full ranges of flexion, extension, and lateral bending. The pedicle portions of vertebrae have traditionally provided excellent points to connect spinal rod and screw fixation systems because the pedicles include significant amounts of cortical bone into which a screw may be effectively placed. However, the posterior portion of the spine supported by fixation systems using pedicle screws is not the predominant natural load bearing structure of an anatomically correctly functioning spine. Therefore, a dynamic system that relies on pedicle screws may need a dynamic or flexible device connecting between the pedicle screws that is capable of responding non-linearly to loads applied in order to appropriately shares load with anterior portions of the spine. A need exists for improved pedicle-based implants that may be capable of both supporting a full range of anatomical loads developed over various degrees of flexion, extension, and lateral bending and sharing loads with anterior portions of connected vertebrae in a physiologically appropriate manner.

SUMMARY

An embodiment of the invention is a flexible spinal rod that includes a retainer and a flexible shaft. The retainer may have a first end configured to be coupled with a first pedicle screw and an opposite second end. The flexible shaft may include a first end configured to be coupled with a second pedicle screw and an opposite second end slideably coupled through the second end of the retainer. The flexible shaft of some embodiments is configured to bend to change curvature along at least a portion of a length of the flexible shaft in response to normal physiological loads applied to the flexible spinal rod through the first end of the retainer and the first end of the flexible shaft.

Another embodiment of the invention is a flexible spinal rod that includes a flexible retainer and a shaft. The flexible retainer may include a first end configured to be coupled with a first pedicle screw and an opposite second end. The shaft may include a first end configured to be coupled with a second pedicle screw and an opposite second end slideably coupled through the second end of the flexible retainer. The flexible retainer of some embodiments is configured to bend to change curvature along at least a portion of a length of the flexible retainer in response to normal physiological loads applied to the flexible spinal rod through the first end of the retainer and the first end of the flexible shaft.

Yet another embodiment of the invention is a spinal construct comprising a first pedicle screw, a second pedicle screw, a retainer, and a flexible shaft. The retainer may include a first end configured to be coupled with the first pedicle screw and an opposite second end. The flexible shaft may include a first end configured to be coupled with the second pedicle screw and an opposite second end slideably coupled through the second end of the retainer. In some embodiments, the flexible shaft is configured to bend to change curvature along at least a portion of a length of the flexible shaft in response to normal physiological loads applied to the flexible spinal rod through the first end of the retainer and the first end of the flexible shaft.

DETAILED DESCRIPTION

Figure 1:
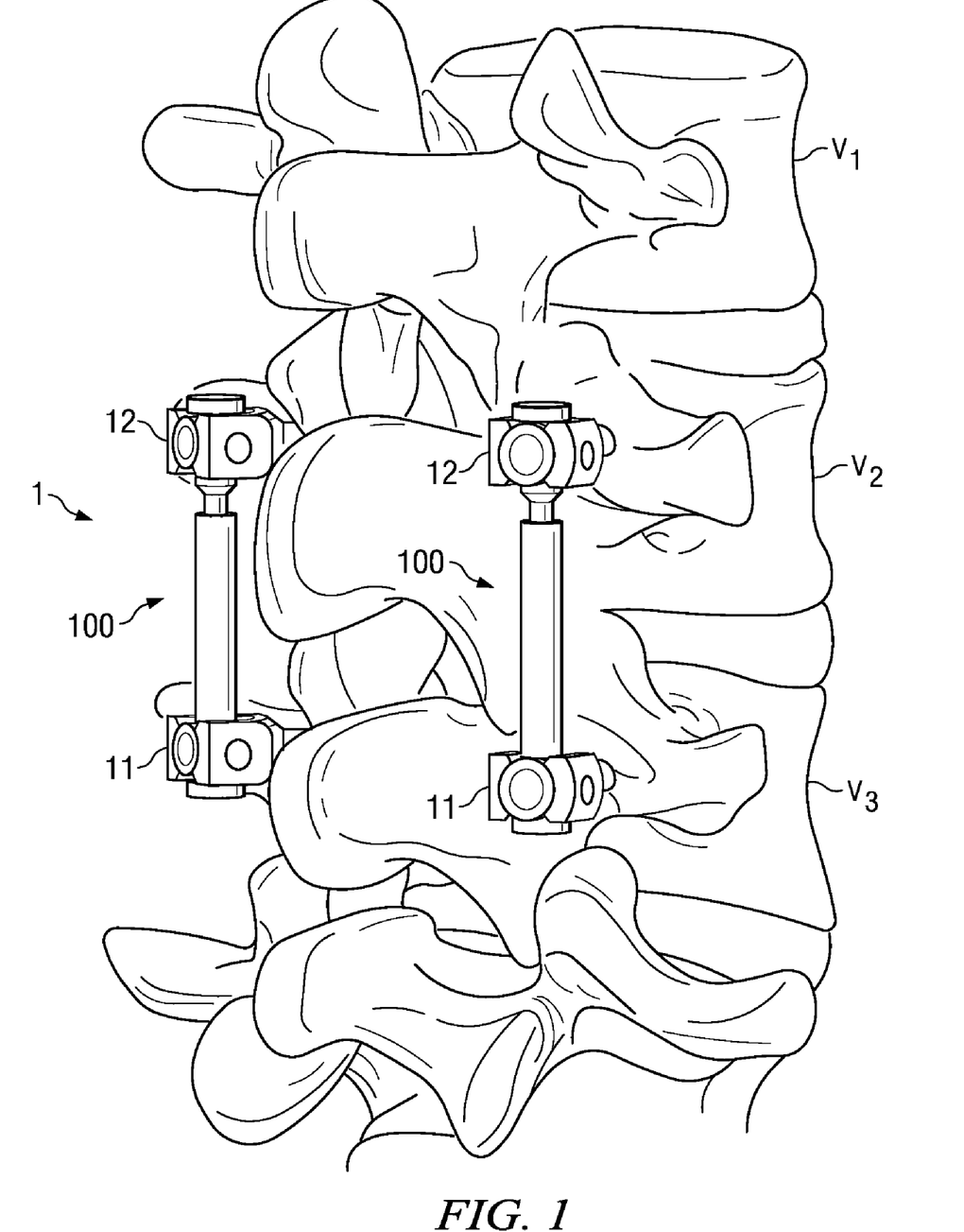
FIG. 1 is a perspective view of embodiments of a spinal construct with flexible spinal rods implanted in a portion of a lumbar region of a spine.
Figures 2, 3:
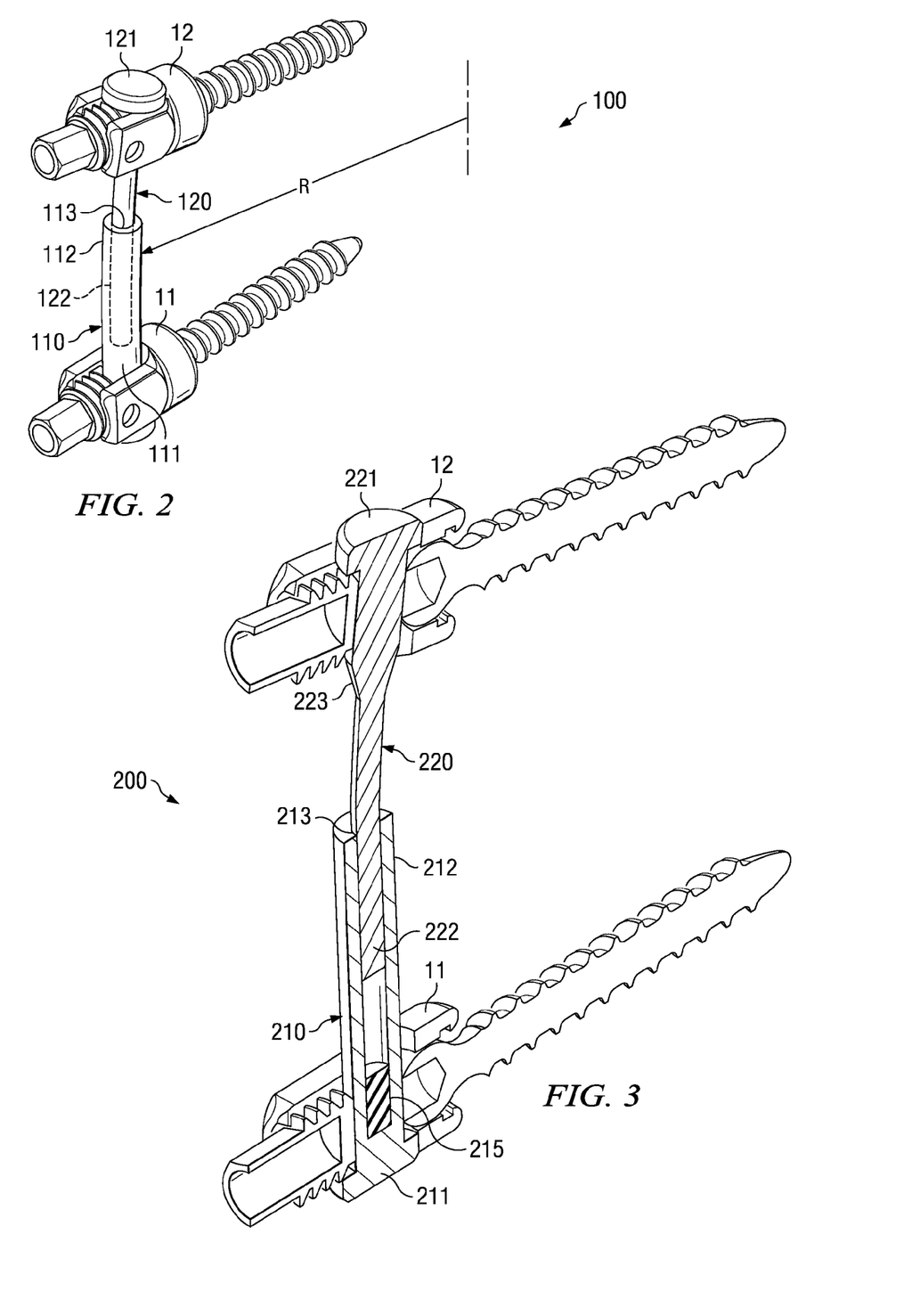
FIG. 2 is a perspective view of an embodiment of a spinal construct with a flexible spinal rod.
FIG. 3 is a cross-sectional view of a perspective view of an embodiment of a spinal construct with a flexible spinal rod.

A spinal construct 1 with flexible spinal rods 100 is illustrated in FIG. 1. Three vertebral bodies $V_1$, $V_2$, and $V_3$ are shown with the spinal construct 1 attached to the vertebral bodies $V_2$, and $V_3$. The spinal construct 1 includes two flexible spinal rods 100, each attached to the vertebral bodies $V_3$ and $V_2$ respectively with a first pedicle screw 11 and a second pedicle screw 12. Each of the flexible spinal rods 100, 300 is shown in a partially expanded state in FIGS. 1, 2, and 4. In FIG. 3, an embodiment of a flexible spinal rod 200 is shown in a mostly expanded state. The pedicle screws 11, 12 may be of any effective type capable of connecting with a vertebra. First and second pedicle screws 11, 12 illustrated may particularly be CD HORIZON® LEGACY™ top-loading pedicle screws supplied by Medtronic, Inc.

The flexible spinal rod 100 illustrated in FIG. 2 includes a retainer 110 and a shaft 120. The retainer 110 illustrated has a first end 111 coupled with the first pedicle screw 11 and an opposite second end 112. The retainer 110 shown is tubular and includes an opening 113 through the tubular shape of the retainer 110 at the second end 112. The illustrated retainer 110 is a circular tubular shape, but in other embodiments various tubular shapes may include an exterior cross-section or an opening of any functional shape. Non-limiting examples of functional shapes for the retainer 110 or the flexible shaft 120 are disclosed in U.S. Pat. Appl., Publication No. 2007/0191841, entitled, "Spinal Rods Having Different Flexural Rigidities about Different Axes and Methods of Use" which is hereby incorporated by reference in its entirety herein. The outside diameter of embodiments of the retainer may be between about 3 mm and about 20 mm. The outside diameter of still other embodiments may be more particularly between about 4 mm and about 7 mm.

Embodiments of the retainer may be straight or may include a curvature or a compound curvature along a length of the retainer. For example, the retainer 110 has a curvature with a radius of "R" with a concavity in the direction of a vertebral structure to which it is configured to be attached. The radius of curvature may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant. The opening 113 in the illustrated retainer 110 is a single opening and is centered through a cross-section of the retainer 110. However, in other embodiments, the opening 113 may include multiple openings and alternatively or in addition may be offset from the center of the cross-section of the retainer 110.

In some embodiments, the retainer 110 is configured to bend to change curvature along at least a portion of a length of the retainer 110 in response to normal physiological loads applied to the flexible spinal rod 100 through the first and second pedicle screws 11, 12. A retainer under various embodiments may be changed from a curved state to a different curved state, may be changed from a straight state to a curved state, or may be changed from a curved state to a straight state. The extent of change in curvature may be between about 2 degrees and about 25 degrees. As used herein, a "normal physiological load" is a load that results from loads and motions applied to a typical spinal segment of an average weight person taking part in normal activities that may flex, extend, laterally bend, or vertically or laterally load and unload a spinal segment. In the illustrated embodiment, load is applied to the flexible spinal rod 100 through the first end 111 of the retainer 110 that couples with the first pedicle screw 11 and through a first end 121 of the flexible shaft 120 that couples with the second pedicle screw 12. The first and second pedicle screws 11, 12 are coupled to vertebrae from which load is transferred.

A flexible shaft 120 is illustrated in FIG. 2. The first end 121 of the flexible shaft 120 may be configured to be coupled with the second pedicle screw 12 and an opposite second end 122 that is slideably coupled through the opening 113 in the second end 112 of the retainer 110. The illustrated flexible shaft 120 has a round cross-sectional shape. In other embodiments, various cross-sectional shapes may be used. As noted above, non-limiting examples of cross-sectional shapes for the flexible shaft 120 with various structural characteristics are disclosed in U.S. Pat. Appl., Publication No. 2007/0191841. The outside diameter of embodiments of the flexible shaft 120 may be between about 1 mm and about 18 mm. The outside diameter of still other embodiments may be more particularly between about 2 mm and about 5 mm. Embodiments of a flexible shaft 120 may have various non-symmetrical cross-sectional shapes that provide more resistance to loading in one direction than in another direction.

The illustrated flexible shaft 120 fits within the retainer 110 with a small tolerance between the flexible shaft 120 and the retainer 110. A small tolerance may result in some frictional resistance between the flexible shaft 120 and the retainer 110. In other embodiments where a larger tolerance is present, or where materials with smaller coefficients of friction are present, less frictional resistance between the flexible shaft 120 and the retainer 110 is created. In some embodiments of a retainer, the retainer may include a notch in which a portion of the flexible shaft is configured to slide. Similarly, some embodiments of a flexible shaft may include a notch in which a portion of the retainer is configured to slide. An embodiment may include a retainer and a flexible shaft that both include notches in which parts of the other cooperatively slide. The notches of some embodiments of one or both of a flexible shaft and a retainer may, for example, be in the shape of a dovetail joint, a round section, a polygonal section, an interlocking of flat sections, any section including re-entrant angular cuts, or any combination of the specified example shapes.

Embodiments of the flexible shaft may be straight or may include a curvature or a compound curvature along a length of the flexible shaft. For example, the flexible shaft 120 is shown with a curvature that substantially matches the curvature of the retainer 110 and has a radius of "R" with a concavity in the direction of a vertebral structure to which it is configured to be attached. The retainer 110 and the flexible shaft 120 are curved when in an unloaded state. The radius of curvature may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant.

The flexible shaft 120 of some embodiments is configured to bend to change curvature along at least a portion of the length of the flexible shaft 120 in response to normal physiological loads applied to the flexible spinal rod 100. In the illustrated embodiment, load is applied to the flexible spinal rod 100 through the first end 111 of the retainer 110 that couples with the first pedicle screw 11 and through the first end 121 of the flexible shaft 120 that couples with the second pedicle screw 12. The first and second pedicle screws 11, 12 are coupled to vertebrae from which load is transferred. A flexible shaft under various embodiments may be changed from a curved state to a different curved state, may be changed from a straight state to a curved state, or may be changed from a curved state to a straight state. The extent of change in curvature may be between about 2 degrees and about 25 degrees.

Because one or both of a retainer and a shaft may be flexible, the spinal construct of some embodiments is capable of flexing to approximately track a center of rotation of spinal segments that moves under various loading conditions and conditions of spinal movement. Deformation of the flexible material permits a flexible spinal rod to more closely follow the motion and load bearing characteristics of a natural spinal segment, including sharing load with anterior portions of the vertebrae, rather than dictating a more rigidly defined path of motion of a spinal segment in combination with a more rigid implant. Particular responses to loads and movements, such as but not limited to, flexion, extension, and lateral bending may be achieved by altering the cross-sectional shapes, the materials, the tolerances between, and the lengths of one or both of a retainer and a shaft. One or both of the material and the cross-sectional shape of embodiments of a flexible shaft or a retainer may be altered along the length of the flexible shaft to provide different strength and deflection characteristics at different states of expansion of a flexible spinal rod. Note that in some embodiments, a shaft in the position of the flexible shaft 120 of FIG. 2, or other specified flexible shaft, may not be flexible under the terms herein, but may instead be rigid.

The flexible spinal rod 100 may also include one or more dampening elements between the retainer 110 and the flexible shaft 120. The dampening elements may, by way of example, take the form of resilient materials or bumpers. In some embodiments, resilient materials are included in the flexible spinal rod 100 in positions where the resilient materials will be compressed or stretched between the retainer 110 and the flexible shaft 120 near one or both of the maximum and minimum lengths of the spinal rod 100. Such a construct may provide a non-linear force/displacement profile that approximately mimics the resistance normally experienced by a natural spinal segment.

Figure 5:
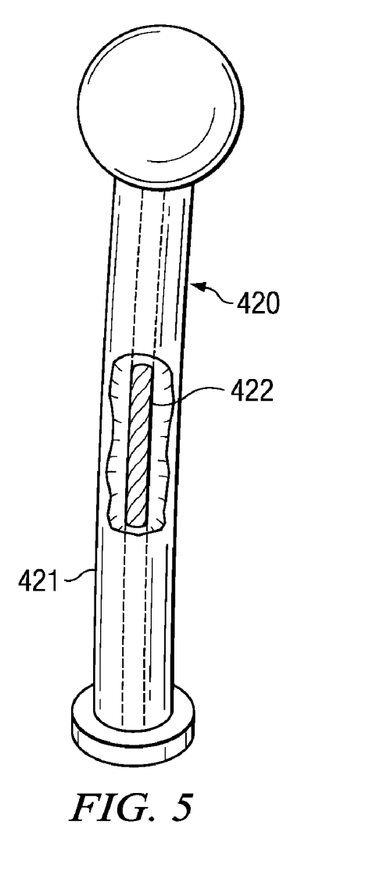
FIG. 5 is a perspective view of a shaft of an embodiment of a flexible spinal rod having a partial cut-away to view various internal components.

Various embodiments of a retainer or a shaft may be made from any biocompatible material. For example and without limitation, one or both of a retainer and a shaft may include in whole or in part: non-reinforced polymers, reinforced polymers, metals, ceramics and combinations of these materials. Reinforcing of polymers may be accomplished with carbon, metal, or glass fibers or any other effective fiber material. In some embodiments, one or both of a retainer and a shaft may include sections of bone or other tissues. Tissue materials include, but are not limited to, autograft, allograft, or xenograft, and may be resorbable or non-resorbable in nature. Examples of other tissue materials include connective tissues, demineralized bone matrix, and combinations of these and other materials. Biocompatible polymers may be obtained from natural or synthetic sources. Examples of natural materials of which a polymer may be composed include collagen, elastin, silk, and demineralized bone matrix. Examples of biocompatible polymer materials include polyethylene, low density polyethylene, polymethylmethacrylate (PMMA), polyetheretherketone (PEEK), polyetherketoneketone (PEKK), and polyurethane. A biocompatible polymer may also include a polymeric hydroxyethylmethacrylate (PHEMA). Example biocompatible metals include stainless steel and other steel alloys, cobalt chrome alloys, tantalum, titanium, titanium alloys, titanium-nickel alloys such as Nitinol and other superelastic or shape-memory metal alloys. Where a retainer or a shaft is designed to be flexible, at least a portion of one or both of the retainer and the shaft may comprise PEEK, Nitinol, or a braided core, such as a cord of braided Dacron® material (Dacron is a registered trademark of Invista, Inc.), that has been overmolded with ultra-high molecular weight polyethylene (UHWPE), polyurethane, or other structural polymer. An example device is illustrated in FIG. 5 by a flexible shaft 420 including at least a braided core 422 and an overmolding 421. The braided core 422 of some embodiments is braided at least in part from Dacron® material and the overmolding 421 includes UHWPE. In some embodiments, the retainer 110 comprises Type 2 anodized titanium that at least in part contacts the flexible shaft 120 where the retainer 110 slideably couples with the flexible shaft 120. In this and other embodiments, the flexible shaft 120 may comprise PEEK material.

A cross-section through a perspective view of an embodiment of a flexible spinal rod 200 is shown in FIG. 3. The flexible spinal rod 200 illustrated includes a retainer 210 and a shaft 220. The flexible spinal rod 200 illustrated is in a relatively expanded state and is consistent with a device implanted in a patient that is undergoing flexion of the spine.

The retainer 210 illustrated has a first end 211 coupled with the first pedicle screw 11 and an opposite second end 212. The retainer 210 shown is tubular and includes an opening 213 through the tubular shape of the retainer 210 at the second end 212. The illustrated retainer 210 is a circular tubular shape, but in other embodiments various tubular shapes may include an exterior cross-section or an opening of any functional shape. Non-limiting example shapes and sizes are noted above with reference to the retainer 110, and may equally apply to the retainer 210.

Embodiments of the retainer may be straight or may include a curvature or a compound curvature along a length of the retainer. For example, the retainer 210 is straight. The straight configuration or a radius of curvature may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant. The opening 213 in the illustrated retainer 210 is a single opening and is centered through a cross-section of the retainer 210. However, in other embodiments, the opening 213 may include multiple openings and alternatively or in addition may be offset from the center of the cross-section of the retainer 210.

In some embodiments, the retainer 210 is configured to bend to change a curvature along at least a portion of a length of the retainer 210 in response to normal physiological loads applied to the flexible spinal rod 200 through the first and second pedicle screws 11, 12. Bendable retainer attributes are detailed above for the retainer 110, and may equally apply to the retainer 210. The retainer 210 is shown in a straight configuration and is not necessarily configured to bend to change curvature. A retainer that does not bend under normal physiological loads may be useful to particularly control an expansion path of a flexible spinal rod of some embodiments, and may be used in combination with a flexible or inflexible shaft.

A flexible shaft 220 is illustrated in FIG. 3. The first end 221 of the flexible shaft 220 may be configured to be coupled with the second pedicle screw 12. An opposite second end 222 is shown slideably coupled through the opening 213 in the second end 212 of the retainer 210. The illustrated flexible shaft 220 has a round cross-sectional shape. In other embodiments, cross-sectional shapes of any functional shape may be used. Non-limiting example shapes and sizes are noted above with reference to the flexible shaft 120, and may equally apply to the flexible shaft 220.

The illustrated flexible shaft 220 includes a taper 223 from a larger diameter where the flexible shaft 220 couples with the second pedicle screw 12 to a smaller diameter toward the second end 222 of the flexible shaft 220. The taper 223 may be gradual over a relatively long portion of the flexible shaft 220, or may exist only over a short portion of the length of the flexible shaft 220. Various tapers that increase and decrease the diameter of a shaft may exist to provide particular strength characteristics at various states of expansion of the flexible spinal rod 200. The taper 223 of some embodiments is configured to act in cooperation with the opening 213 to resist forces tending to compress the flexible spinal rod 200 along its length. In some embodiments, the opening 213 is fluted to contact the taper 223 over a larger surface area. One or both of the taper 223 and the opening 213 may include bumpers or resilient materials that dampen compression of the flexible spinal rod 200. The flexible shaft 220 may fit within the retainer 210 with a small tolerance between the flexible shaft 220 and the retainer 210 in some embodiments. A small tolerance may result in some frictional resistance between the flexible shaft 220 and the retainer 210. In other embodiments where a larger tolerance is present, or where materials with smaller coefficients of friction are present, less frictional resistance between the flexible shaft 220 and the retainer 210 is created.

The flexible shaft 220 is shown with a curvature in portions of the flexible shaft 220 that are outside of the retainer 210. In the illustrated embodiment, the retainer 210 forces the flexible shaft 220 to assume the curvature of the retainer 210 (the retainer 210 is straight in this embodiment) where the flexible shaft 220 is within the retainer 210 and fits with the retainer 210 with a small tolerance. The flexible shaft 220 of the illustrated embodiment may be curved when in an unloaded state. A curved flexible shaft 220 that is forced to a different curvature within the retainer 210 may create additional resistance to movement between the flexible shaft 220 and the retainer 210. Therefore, difference in curvature between a retainer and a shaft may be an additional design variable for controlling the force/displacement characteristics of a flexible spinal rod. Radius of curvature of one or both of the retainer 210 and the flexible shaft 220 may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant.

The flexible shaft 220 of some embodiments is configured to bend to change curvature along at least a portion of the length of the flexible shaft 220 in response to normal physiological loads applied to the flexible spinal rod 200 through the first and second pedicle screws 11, 12. Bendable shaft attributes are detailed above for the flexible shaft 120 and are equally applicable to the flexible shaft 220.

The flexible spinal rod 200 may also include one or more dampening elements between the retainer 210 and the flexible shaft 220. The dampening elements may take the form of resilient materials or bumpers. In some embodiments, resilient materials are included in the flexible spinal rod 200 in positions where the resilient materials will be compressed or stretched between the retainer 210 and the flexible shaft 220 near one or both of the maximum and minimum lengths of the spinal rod 200. Such a construct may provide a non-linear force/displacement profile that approximately mimics the resistance normally experienced by a natural spinal segment. For example, a bumper 215 is illustrated within the retainer 210 near the first end 211 of the retainer 210. When the flexible spinal rod 200 is moved near a state of full compression, or minimum length, the bumper 215 is compressed between the retainer 210 and the second end 222 of the flexible shaft 220. Where the bumper 215 is made from a resilient material and movement between the retainer 210 and the flexible shaft 220 is resisted by a progressively larger opposite force generated in the bumper 215, a non-linear force/displacement profile that approximately mimics the resistance normally experienced by a natural spinal segment is provided by the flexible spinal rod 200.

Figure 4:
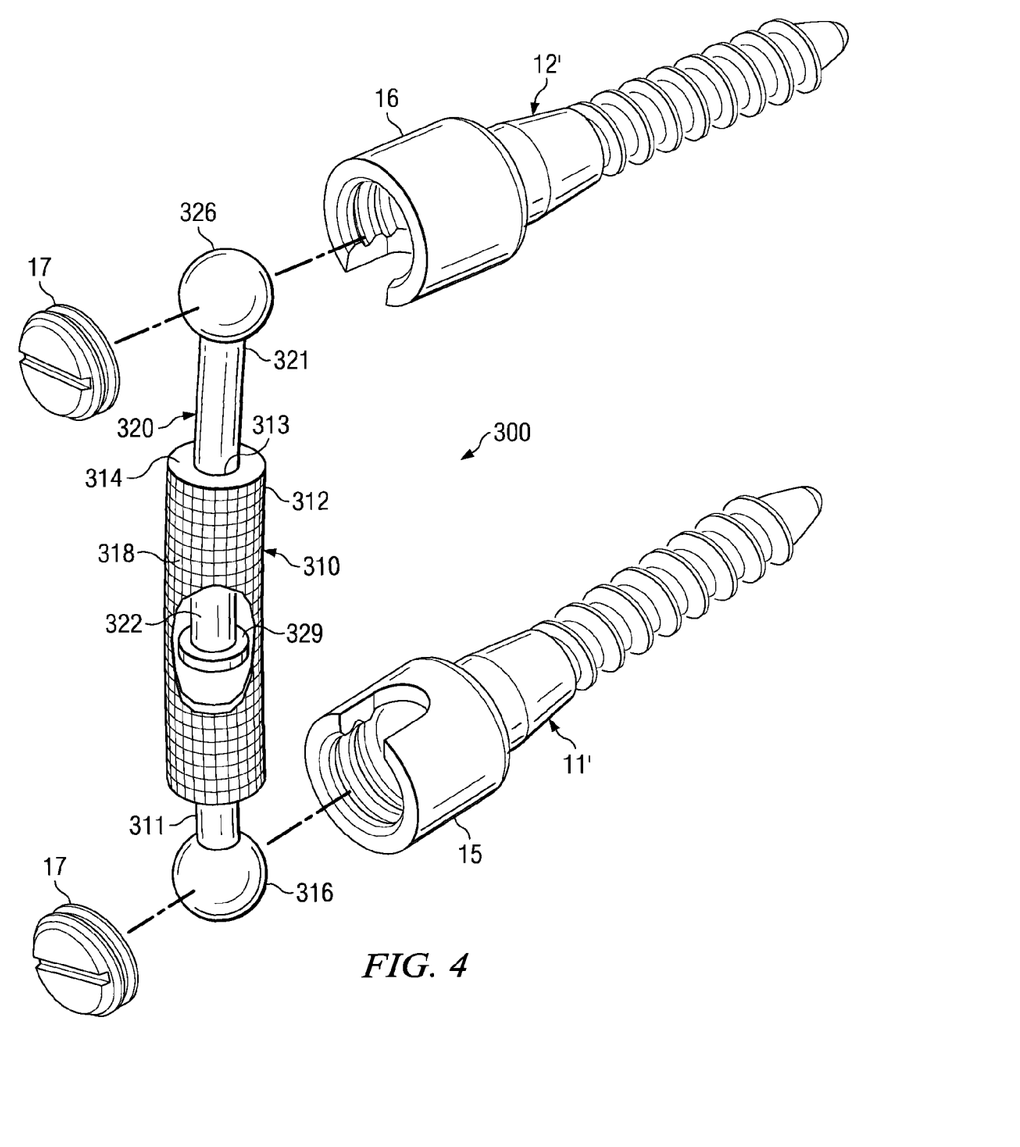
FIG. 4 is an exploded perspective view of an embodiment of a spinal construct with a flexible spinal rod having a partial cut-away to view various internal components.

An exploded perspective view of an embodiment of a spinal construct with a flexible spinal rod 300 is shown in FIG. 4. A partial cut-away of a portion of the retainer 310 is shown to view various internal components. The flexible spinal rod 300 illustrated includes a retainer 310 and a flexible shaft 320. The retainer 310 shown has a first end 311 configured to couple with a first pedicle screw 11' and an opposite second end 312.

The coupling mechanism between the first end 311 of the retainer 310 and the first pedicle screw 11' allows for three degrees of rotational freedom between the retainer 310 and the first pedicle screw 11'. In the embodiment shown, the first end 311 of the retainer 310 includes a ball 316 configured to fit in a receiver 15 of the first pedicle screw 11'. An end cap 17 fits over the ball 316 to enclose the ball 316 within the receiver 15, but allows the ball 316 to rotate within the receiver 15. Coupling mechanisms of other embodiments may provide a hinge that allows one degree of rotational freedom or a guided hinge that allows two degrees of rotational freedom. Other embodiments may alternatively or in combination include couplings that allow limited translation between a flexible spinal rod and a pedicle screw.

The retainer 310 shown comprises a mesh body 318. The mesh body 318 may be constructed from strands or fibers. The strands or fibers may be any biocompatible material. The strands or fibers may be, without limitation, woven, welded, looped around one another, or embedded in a material that forms a tubular enclosure or partial enclosure. One or both of the materials and orientations of the fibers may be altered to alter the mechanical properties of the retainer 310. For example and without limitation, some embodiments may be strengthened lengthwise to provide greater resistance to spinal flexion, or an embodiment may be configured to be resilient lengthwise to additionally dampen implant resistance near full spinal flexion. The illustrated retainer 310 with mesh body 318 is generally tubular and includes a cap 314 over the second end 312 of the retainer 310. The cap 314 includes an opening 313. The illustrated retainer 310 is a circular tubular shape with a mesh body 318, but in other embodiments various tubular shapes may include an exterior cross-section or an opening of any functional shape. Non-limiting example shapes and sizes are noted above with reference to the retainer 110, and may equally apply to the retainer 310. Further, the retainer 310 may not include a mesh body 318 in some embodiments, but may be constructed of non-mesh materials.

Figure 6:
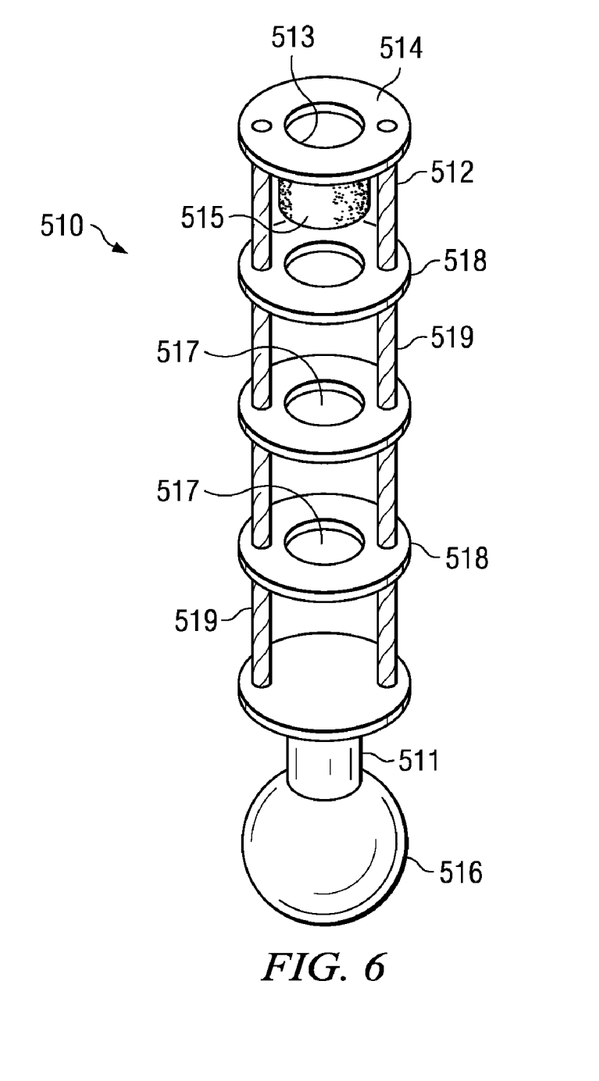
FIG. 6 is a perspective view of a retainer of an embodiment of a flexible spinal rod.

Another embodiment of a retainer is illustrated in FIG. 6. As shown, a retainer 510 includes a first end 511 configured to couple with a first pedicle screw 11' and an opposite second end 512. The coupling mechanism between the first end 511 of the retainer 510 and the first pedicle screw 11' is essentially similar to the coupling mechanism between the first end 311 of the retainer 310 and the pedicle screw 11'. A ball 516 is included at the first end 511. The retainer 510 shown comprises annular members 518 and a cap 514 coupled together with strands 519. Each annular member 518 includes a hole 517. The cap 514 includes an opening 513 through which a shaft may be received. The number, size, shape, strength, and flexibility of each of the annular member 518, the cap 514, and the strands 519 may be altered to provide different strength and deflection characteristics for the retainer 510 as whole. Each of the annular member 518, the cap 514, and the strands 519 may comprise any biocompatible material.

Embodiments of a retainer may be straight or may include a curvature or a compound curvature along a length of the retainer. Returning to FIG. 4 for example, the retainer 310 has a curvature with a concavity in the direction of a vertebral structure to which it is configured to be attached. A straight configuration or a radius of curvature may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant. The opening 313 is a single opening and is centered in the cap 314 and through a cross-section of the retainer 310. However, in other embodiments, the opening 313 may include multiple openings and alternatively or in addition may be offset from the center of the cross-section of the retainer 310.

In some embodiments, the retainer 310 is configured to bend to change a curvature along at least a portion of a length of the retainer 310 in response to normal physiological loads applied to the flexible spinal rod 300 through the first and second pedicle screws 11', 12'. Bendable retainer attributes are detailed above for the retainer 110 and are equally applicable to various embodiments of the retainer 310.

A flexible shaft 320 is illustrated in FIG. 4. A first end 321 of the flexible shaft 320 may be configured to be coupled with a second pedicle screw 12'. The coupling mechanism between the first end 321 of the flexible shaft 320 and the second pedicle screw 12' allows for three degrees of rotational freedom between the flexible shaft 320 and the second pedicle screw 12'. In the embodiment shown, the first end 321 of the flexible shaft 320 includes a ball 326 configured to fit in a receiver 16 of the second pedicle screw 12'. An end cap 17 fits over the ball 326 to enclose the ball 326 within the receiver 16, but allows the ball 326 to rotate within the receiver 16. Coupling mechanisms of other embodiments may provide a hinge that allows one degree of rotational freedom or a guided hinge that allows two degrees of rotational freedom. Other embodiments may alternatively or in combination include couplings that allow limited translation between a flexible spinal rod and a pedicle screw.

An opposite second end 322 of the flexible shaft 320 is shown slideably coupled through the opening 313 in cap 314. The illustrated flexible shaft 320 has a round cross-sectional shape. In other embodiments, cross-sectional shapes of any functional shape may be used. Non-limiting example shapes and sizes are noted above with reference to the flexible shaft 120, and may equally apply to the flexible shaft 320.

Embodiments of the shaft may be straight or may include a curvature or a compound curvature along a length of the shaft. For example, the flexible shaft 320 has a curvature with a concavity in the direction of a vertebral structure to which it is configured to be attached when in an unloaded state. A straight configuration or a radius of curvature may be chosen to treat a particular pathology or to match rotational characteristics of a spinal segment, such as but not limited to, matching a particular natural center of rotation. The curvature chosen may also be selected so that a flexible spinal rod works cooperatively with one or more additional implants, such as but not limited to, an arthroplasty implant, an interspinous process implant, and a facet replacement implant.

The flexible shaft 320 of some embodiments is configured to bend to change curvature along at least a portion of the length of the flexible shaft 320 in response to normal physiological loads applied to the flexible spinal rod 300 through the first and second pedicle screws 11', 12'. Bendable shaft attributes are detailed above for the flexible shaft 120 and are equally applicable to the flexible shaft 320.

The flexible spinal rod 300 may also include one or more dampening elements between the retainer 310 and the flexible shaft 320. The dampening elements may take the form of resilient materials or bumpers. In some embodiments, resilient materials are included in the flexible spinal rod 300 in positions where the resilient materials will be compressed or stretched between the retainer 310 and the flexible shaft 320 near one or both of the maximum and minimum lengths of the spinal rod 300. Such a construct may provide a non-linear force/displacement profile that approximately mimics the resistance normally experienced by a natural spinal segment. For example, a bumper (not shown) may be placed within the mesh body 318 of the retainer 310 near the first end 311. When the flexible spinal rod 300 is moved near a state of full compression, or minimum length, the bumper is compressed between the retainer 310 and the second end 322 of the flexible shaft 320. Similarly, a bumper (not shown) may be placed within the mesh body 318 of the retainer 310 inside of the cap 314. The cap 314 in combination with a shoulder 329 near the second end of the flexible shaft 320 serves as a stop to prevent sliding of at least a portion of the flexible rod 310 past the cap 314. In this and other embodiments, the shoulder 329 is a catch for engaging a portion or the retainer 310 to prevent sliding of at least a portion of the flexible rod 320 past the second end 312 of the retainer 310. Additionally, when the flexible spinal rod 300 is moved near a state of full expansion, or maximum length and includes a bumper inside the cap 314, the bumper is compressed between the cap 314 of the retainer 310 and the shoulder 329 on the flexible shaft 320. The retainer 510 illustrated in FIG. 6 also includes a bumper 515 within the retainer 510 near the second end 512 and inside of the cap 514. The cap 514 in combination with an element such as the shoulder 329 near the second end of the flexible shaft 320 serves as stop to prevent sliding of at least a portion of a flexible rod past the cap 514. When a flexible spinal rod employing the retainer 510 is moved near a state of full expansion, or maximum length and includes the bumper 515 inside the cap 514, the bumper 515 may be compressed between the cap 514 of the retainer 510 and a shoulder or other component on a flexible shaft.

In other embodiments, one or more bumpers may be attached near the second end 322 of the flexible shaft 320 in position to be compressed between elements near the first or second ends 311, 312 of the retainer 310. Where the one or more of the bumpers detailed above is made from a resilient material and movement between the retainer 310 and the flexible shaft 320 is resisted by a progressively larger opposite force generated in the bumper, a non-linear force/displacement profile that approximately mimics the resistance normally experienced by a natural spinal segment is provided by the flexible spinal rod 300.

Any of the bumpers noted above may be made from a resilient material. In some embodiments, a bumper is a solid material. A bumper may also comprise a fluid material, or may be placed as a liquid and then harden to a solid over time or as a result of some other stimulus, such as but not limited to, a second chemical part, heat, removal of heat, and electromagnetic energy. Non-limiting example materials from which a bumper may be made include silicone, silicone-polyurethane, polyurethane, polyolefin rubbers, hydrogels, Nitinol or other superelastic alloys, and a gas contained within a vessel or within various components of a flexible spinal rod.

In some embodiments, the distance of longitudinal expansion and contraction of a flexible spinal rod is a distance greater than about 5 mm. Particularly, the distance of longitudinal expansion may be about 5-15 mm. It may be significant for some embodiments to provide an adequate distance of longitudinal expansion to enable more physiologically accurate spinal constructs. The range of flexion-extension motion permitted by some embodiments is about 2-25 degrees.

Terms such as inside, outside, anterior, posterior, and the like have been used relatively herein. However, such terms are not limited to specific coordinate orientations, but are used to describe relative positions referencing particular embodiments. Such terms are not generally limiting to the scope of the claims made herein. Any embodiment or feature of any pedicle screw 11, 11', 12, 12', or any flexible spinal rod 100, 200, 300, or any other component shown or particularly described herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A flexible spinal rod comprising:
    a retainer with a first end coupled with a first pedicle screw and an opposite second end;
    a flexible shaft with a first end coupled with a second pedicle screw and an opposite second end slideably coupled through the second end of the retainer; and
    a shoulder near the second end of the flexible shaft configured to prevent sliding of at least a portion of the flexible shaft;
    wherein the flexible shaft is configured to bend to change curvature along at least a portion of a length of the flexible shaft in response to normal physiological loads applied to the flexible spinal rod through the first end of the retainer and the first end of the flexible shaft;
    wherein the flexible shaft and retainer are curved when in an unloaded state;
    wherein the opposite second end of the flexible shaft is a portion of the flexible shaft that is configured to bend to change curvature in response to normal physiological loads applied to the flexible spinal rod through the first end of the retainer and the first end of the flexible shaft; and
    wherein the retainer includes a spherical coupling mechanism configured to couple with the first pedicle screw that allows one or more degrees of rotational freedom between the retainer and the first pedicle screw.

2. The flexible spinal rod of claim 1, further comprising an end cap configured to enclose the coupling mechanism within at least a portion of the first pedicle screw, while allowing the coupling mechanism to rotate within the at least a portion of the first pedicle screw wherein the shoulder serves as a stop to prevent sliding of at least a portion of the flexible shaft past the end cap.

3. The flexible spinal rod of claim 1 wherein the retainer is tubular and is configured to receive the flexible shaft within an opening through the tubular shape of the retainer.

4. The flexible spinal rod of claim 1 wherein the retainer includes a stop near the second end of the retainer that in combination with the shoulder prevents sliding of the at least a portion of the flexible shaft past the stop.

5. The flexible spinal rod of claim 4 wherein the stop is a cap on the second end of the retainer that covers at least a portion of a cannula through the retainer.

6. The flexible spinal rod of claim 1 wherein the retainer comprises titanium and includes a Type 2 anodized titanium area at least where the retainer slideably couples with the flexible shaft.

7. The flexible spinal rod of claim 1 wherein the retainer comprises two or more rings connected to one another by at least one strand.

8. The flexible spinal rod of claim 1 wherein the retainer comprises a mesh body.

9. The flexible spinal rod of claim 1 wherein the retainer includes a notch in which a portion of the flexible shaft is configured to slide.

10. The flexible spinal rod of claim 1 wherein the flexible shaft includes a spherical coupling mechanism for the second pedicle screw that allows one or more degrees of rotational freedom between the flexible shaft and the second pedicle screw.

11. The flexible spinal rod of claim 1 wherein the flexible shaft includes a round cross-sectional shape.

12. The flexible spinal rod of claim 1 wherein the flexible shaft includes a non-symmetrical cross-sectional shape.

13. The flexible spinal rod of claim 1 wherein the flexible shaft includes a catch for engaging a portion of the retainer to prevent sliding of at least a portion of the flexible rod past the second end of the retainer.

14. The flexible spinal rod of claim 1 wherein the flexible shaft includes a notch in which a portion of the retainer is configured to slide.

15. The flexible spinal rod of claim 1 wherein the flexible shaft comprises PEEK material.

16. The flexible spinal rod of claim 1 wherein the flexible shaft comprises a braided core overmolded with a polymer material.

17. The flexible spinal rod of claim 1, further comprising a bumper between the flexible shaft and the retainer.

18. The flexible spinal rod of claim 1 wherein the retainer is configured to bend to change curvature along at least a portion of a length of the retainer in response to normal physiological loads applied to the flexible spinal rod through the first end of the retainer and the first end of the flexible shaft.

19. A flexible spinal rod comprising:
    a flexible retainer with a first end coupled with a first pedicle screw and an opposite second end;
    a flexible shaft with a first end including a ball coupled with a second pedicle screw and an opposite second end slidably coupled through the second end of the retainer; and
    a shoulder near the second end of the flexible shaft configured to prevent sliding of at least a portion of the flexible shaft;
    wherein the flexible retainer is configured to bend to change curvature along at least a portion of a length of the flexible retainer in response to normal physiological loads applied to the flexible spinal rod through the first end of the flexible retainer and the first end of the flexible shaft;
    wherein the flexible shaft and the flexible retainer are curved when in an unloaded state and the flexible retainer is configured to bend to change curvature along at least a portion of a length of the flexible retainer in response to normal physiological loads applied to the flexible spinal rod through the first end of the flexible retainer and the first end of the flexible shaft; and
    wherein the flexible retainer includes an end cap fitting over the ball to enclose the ball within the retainer, the end cap including a spherical coupling mechanism configured to couple with the first pedicle screw to allow one or more degrees of rotational freedom between the retainer and the first pedicle screw.

20. The flexible spinal rod of claim 19 wherein the flexible retainer is tubular and is configured to receive the flexible shaft within an opening through the tubular shape of the flexible retainer.

* * * * *